(12) United States Patent
Jurich et al.

(10) Patent No.: US 7,764,823 B1
(45) Date of Patent: Jul. 27, 2010

(54) STAMPING IN-LINE CRACK DETECTION SYSTEM AND METHOD

(75) Inventors: Milan Jurich, Dublin, OH (US); Molly Hamilton, Columbus, OH (US); Shaun McCann, Delaware, OH (US)

(73) Assignee: Honda Motor Co., Ltd., Tokyo (JP)

( * ) Notice: Subject to any disclaimer, the term of this patent is extended or adjusted under 35 U.S.C. 154(b) by 832 days.

(21) Appl. No.: 11/676,145

(22) Filed: Feb. 16, 2007

(51) Int. Cl.
*G06K 9/00* (2006.01)

(52) U.S. Cl. .................. 382/141; 382/152; 356/237.1; 356/237.2

(58) Field of Classification Search .......... 382/141, 382/152, 209, 218; 348/125; 356/237.1, 356/237.2
See application file for complete search history.

(56) References Cited

U.S. PATENT DOCUMENTS

| | | | |
|---|---|---|---|
| 5,539,656 A * | 7/1996 | Annigeri et al. ............ 702/35 |
| 5,960,104 A * | 9/1999 | Conners et al. ............ 382/141 |
| 6,610,953 B1 | 8/2003 | Tao et al. |
| 6,711,284 B1 * | 3/2004 | Koide .................... 382/141 |
| 6,734,383 B1 | 5/2004 | Calcoen et al. |
| 6,840,083 B2 | 1/2005 | Hijikata |
| 6,847,443 B1 | 1/2005 | Herod et al. |
| 6,864,970 B1 | 3/2005 | Ruymen et al. |
| 6,894,772 B2 | 5/2005 | Goetz et al. |
| 6,894,775 B1 | 5/2005 | Cech |
| 7,432,505 B2 * | 10/2008 | Brummel ................. 250/332 |
| 2005/0036135 A1 | 2/2005 | Earthman et al. |
| 2005/0174567 A1 | 8/2005 | Hanna |
| 2006/0222237 A1 * | 10/2006 | Du et al. .................. 382/152 |

* cited by examiner

*Primary Examiner*—John B Strege
(74) *Attorney, Agent, or Firm*—Standley Law Group LLP

(57) ABSTRACT

A system and method for automatically detecting cracks in components produced by a stamping process. A substantially uniform backlighting of the component can be produced, even when direct backlighting is partially blocked by structure used to support the component during inspection. One or more image detectors simultaneously image the component from a top side while it is backlit. One or more images of the current component are then compared to a master image of the component. Light passing through or visible through cracks in the component will cause the system to see a difference between the current image(s) of the component and the master image(s), thereby indicating a crack(s). A user is automatically notified upon detection of a crack.

22 Claims, 8 Drawing Sheets

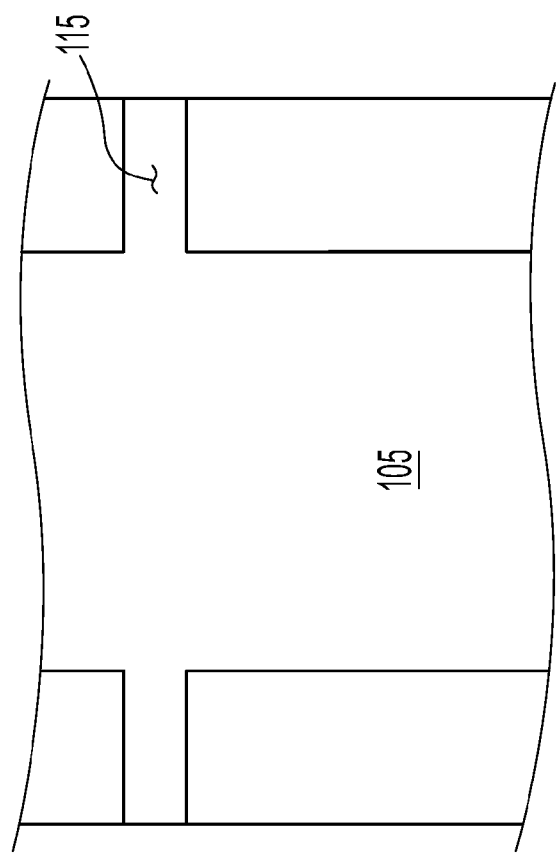
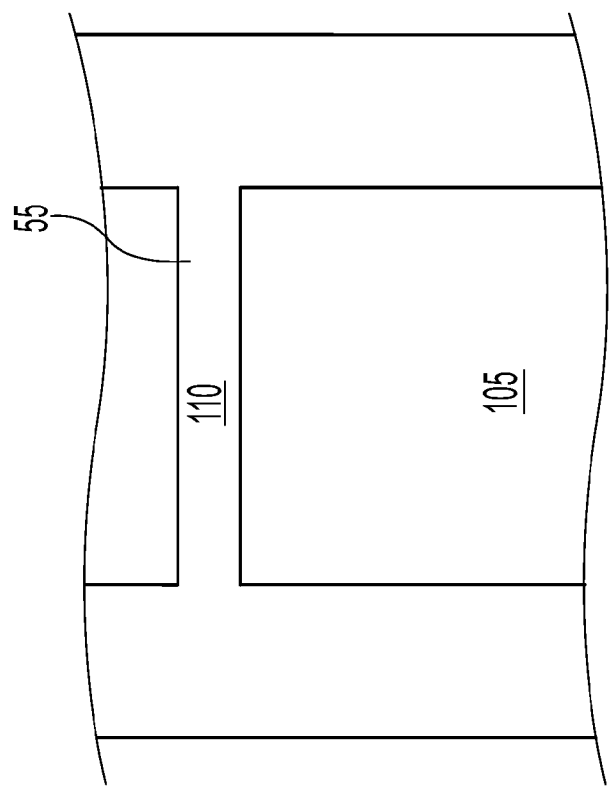
Fig. 5a
Fig. 5b

STAMPING IN-LINE CRACK DETECTION SYSTEM AND METHOD

BACKGROUND

The present invention relates to the detection of cracks and similar defects in stamped parts. More particularly, the present invention relates to the automated detection of cracks and similar defects in stamped parts during the stamping process.

Defects, particularly cracks, are a common problem inherent in component stamping. Such cracks, also commonly referred to as necking or elongation, may occur as a result of forming the material used to make a particular component. Defects in the material itself may also cause or contribute to the existence of cracks. Therefore, as used herein, the term crack shall encompass any type of separation in the material of a stamped component whether caused by the stamping (forming) process, by a deficiency in the physical structure of the material itself, or some combination thereof.

Cracks are problematic because they result in weakened areas that may cause a component to eventually fail during use. These cracks may also be undesirable for cosmetic reasons. Consequently, it is highly desirable that components containing cracks be discovered before being put to an end use or before their joining to other components of a larger assembly.

Discovery of such cracks is difficult, however, because detection is usually accomplished through visual observation of a component of interest. Unfortunately, such cracks are not particularly amenable to visual detection for various reasons. For example, such cracks may, at least initially, be rather small in size. There is generally also no color change or other obvious variation between a crack and the surrounding component material to call attention to the defect. Further, the responsibility for crack detection often falls on the shoulders of a machine operator or another person tasked with such duties—and often must be accomplished very quickly, such as within a single machine cycle.

Additionally, it can be understood by one skilled in the art that, with respect to certain stamping processes such as, for example, a transfer press process, off-line (end of process) inspection may result in excessive scrap. That is, if a crack is being produced early in the stamping process, and inspection cannot be accomplished until the end of the process, a number of additional defective components will have been produced prior to the first defective component reaching the inspection station. Offline component inspection may also add to overall manufacturing cycle time.

Therefore, what is needed is a system and method for automatically detecting cracks in stamped components, preferably within the physical confines and operating parameters of related stamping equipment. A system and method of the present invention satisfies this need.

SUMMARY OF GENERAL INVENTIVE CONCEPT

Generally, the present invention is directed to a system and method of automatically detecting cracks in stamped components, such that defective components are not released for use, or to a downstream process, for example. Preferably, but not necessarily, the crack detection system is installed to and operates within the physical confines of the stamping equipment at issue, as well as within the stamping equipment cycle time. This is beneficial so as to avoid increasing the floor space required for the stamping operation and to prevent an increase in cycle time. It is possible, however, to also install a crack detection system of the present invention so as to perform post-stamping inspection—whether concurrently with an ongoing stamping process or without concern therefor.

Embodiments of the present invention will commonly employ one, and more likely, a plurality of image detectors such as cameras or other vision sensors. One or more light sources are also typically employed to backlight a component during inspection. Specialized software and a user interface is employed to evaluate the image(s) detected by the image detector(s) and present the results to the user of the system.

In certain embodiments of the present invention, side lighting, diffusion tables, lighting enclosures, vibration isolators and various other devices may be used to produce adequate backlighting and accurate imaging of the components of interest.

Preferably, the components that make up a system of the present invention are installed to existing stamping press structure, such that component inspection may be accomplished during the stamping process. Upon detection of one or more cracks in a component, various actions may be taken. For example, equipment may be provided to automatically remove the apparently defective component from the stamping line prior to or after completion of the stamping process. Defective components may be removed to, for example, a defective component area or an area provided for additional inspection. Alternatively, the defective component may simply be identified, such that it may be removed manually at some point during or after the stamping process.

It can be understood from the foregoing that a system and method according to the present invention can have application to a number of different stamping processes. The present invention can be applied to a variety of stamping equipment. For example, and without limitation, the present invention may be used with a standalone press or with a transfer press line. However, in order to further illustrate the construction and operation of such a system and method, a singular example is provided below. In this example, a system and method of the present invention is employed to inspect automotive body panels for cracks. The exemplary system is installed to a stamping transfer press line (i.e., a stamping press line comprising a number of presses arranged in-line, wherein additional forming is performed as a component is transferred from one press to the next during the stamping process).

More specifically, in this particular example, a system for detecting cracks in various automotive body panels is installed within an idle station area existing between two adjacent presses of a transfer press line. Backlighting devices are provided to illuminate the underside of the component while it resides at the idle station. A plurality of overhead vision sensors are also provided to detect any light passing through cracks in the body panels. The vision sensors and backlighting devices may be controlled by a processor. The processor is in communication with specialized software that evaluates images captured by the vision sensors to determine if any cracks are present.

In this particular embodiment, a number of support arms extend across the idle station to provide a rigid surface on which to support the body panels as they travel from the preceding press to the next successive press. These support arms effectively block light from the backlighting devices from reaching corresponding portions of an overlying body panel and, therefore, from illuminating any cracks present in the body panel. Consequently, if only backlighting is employed, the affected areas of the body panel may have cracks that would go undetected by the vision sensors.

Applicants have developed a novel technique for overcoming this problem. Particularly, the upper surfaces of the blocking support arms are preferably provided with an illuminating coating. For example, a coating that absorbs light may be provided when an IR light source will be used, or a coating that reflects light may be provided when a non-IR light source will be used. Additional lighting devices of desired type are then mounted at various locations around the perimeter of the body panel and oriented so as to direct light toward the underside of the body panel and onto the reflective upper surface of the support arms. A diffusion table or similar apparatus is also preferably located subjacent to the support arms such that light emanating from the side mounted lighting devices is spread relatively uniformly along the underside of the body panel. In this manner, the entirety of the underside of the body panel can be illuminated, and the unlit areas of the body panel formerly produced by the support arms are made to effectively disappear. Thus, cracks present in otherwise undetectable portions of the body panel can be detected by the vision sensors.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein:

FIG. 5a shows the blocking effect on crack detection created by certain press structure;

FIG. 5b shows how the system and method of the present invention overcomes this blocking effect;

DETAILED DESCRIPTION OF EXEMPLARY EMBODIMENT(S)

As mentioned above, for purposes of simplicity, a single illustrative and exemplary embodiment of the present invention is discussed in detail below. However, it is to be understood that the present invention is in no way limited by the illustrative embodiment.

Figure 1:
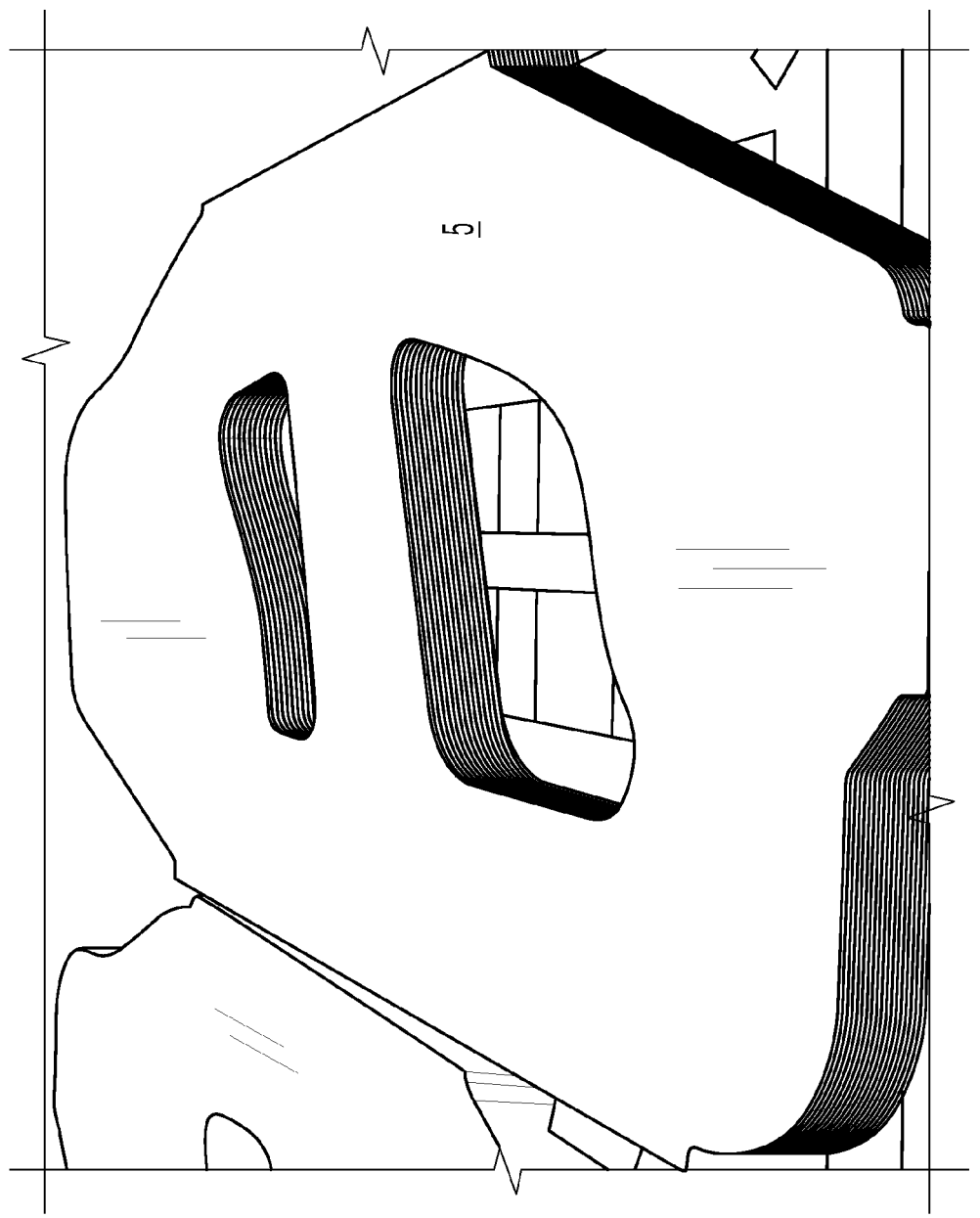
FIG. 1 depicts an exemplary metallic body panel blank.

As can be observed in FIG. 1, this exemplary embodiment of the present invention is designed to inspect a vehicle body panel 5—in this particular case, a vehicle side panel. As shown in FIG. 1, the body panel 5 may still be in blank (unformed) condition as would generally be received from a blanking station. Alternatively, the blank may have already been partially formed by the first draw press 15.

The exemplary embodiment of the present invention is installed to a to a transfer press line 10. The transfer press line 10 employs a number of in-line presses 15, 20, 25, 30 to perform various portions of the overall panel forming process. For example, as can be best observed in FIG. 2, this particular press line performs a draw operation at a first press 15, whereafter the panel is successively transferred to a trim press 20, a bending press 25 and a piercing press 30 (i.e., to individual presses having a trim die, bending die and piercing die, respectively). After operations at the piercing press, the formed panel is successively moved toward an inspection station 35.

With the transfer press line 10 shown, seven body panels 5 must be submitted to the full forming process before the first-formed panel reaches the inspection station 35. Consequently, it can be understood that any cracks produced in the drawing process are not discoverable by an inspector or inspection device located at the inspection station until at least seven panels have been partially or fully formed. It can also be understood, therefore, that early detection of cracks, such as prior to the trim process, can result in a significant reduction of scrap—particularly if the crack(s) are draw process related and likely to be repeated on subsequently drawn panels (e.g., caused by a problem with the draw die, a draw press setting, etc.).

In actuality, it has in fact been found that approximately 95%-98% of cracks appearing in typical body panels will occur as a result of the draw process, with only about 2%-5% of all cracks occurring after the draw process. Therefore, in this embodiment of the present invention, automated crack inspection occurs only between the draw and trim presses 15, 20. Automated crack inspection could occur at another location within the transfer press line 10 but, as can be understood from the foregoing description, may result in a higher scrap rate. Crack detection could also occur at an additional location within or subsequent to the transfer press line 10, but is likely unnecessary.

Figure 2:
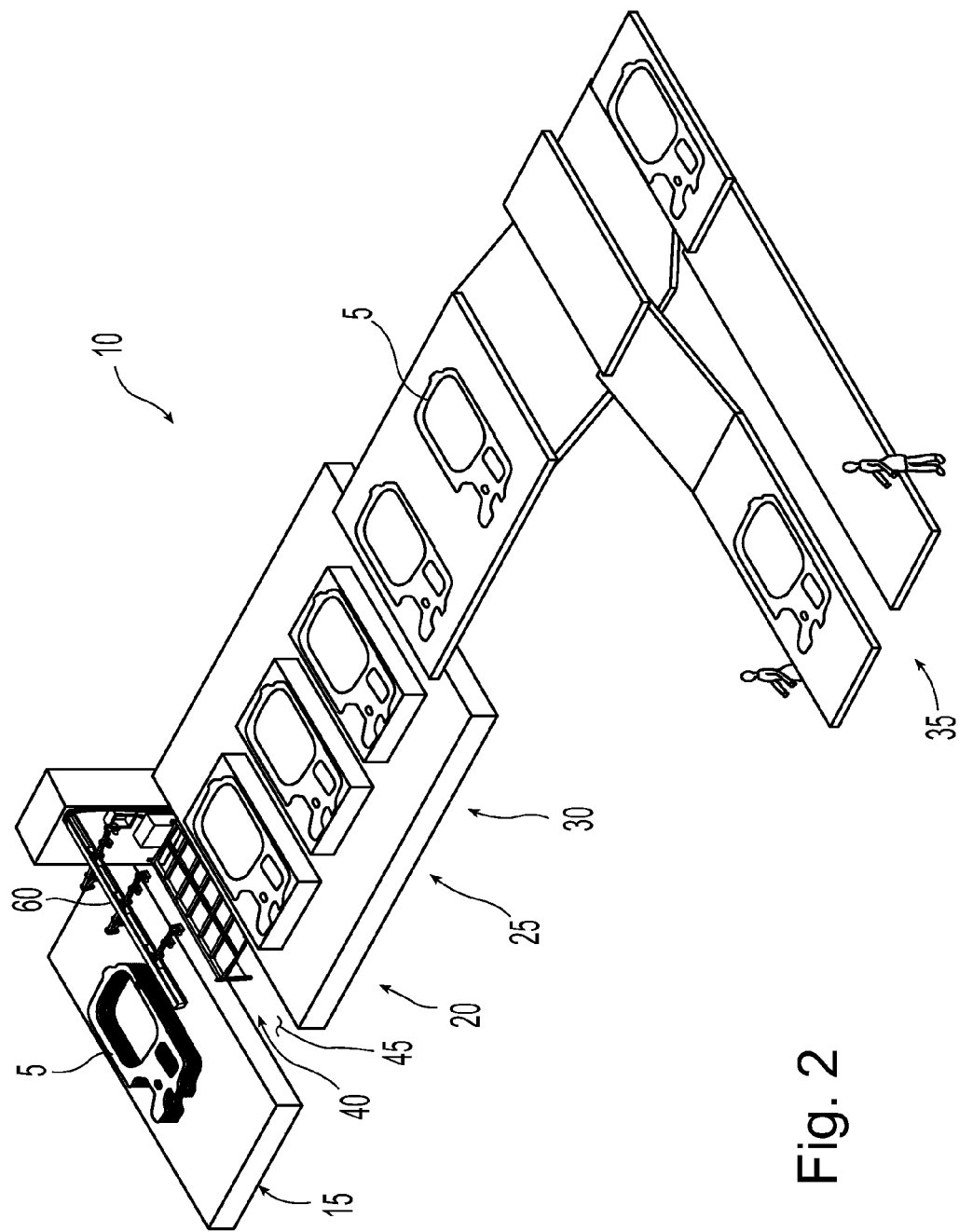
FIG. 2 schematically represents a transfer press line that will further form body panel blanks as shown in FIG. 1 into vehicle body panels.
Figure 3:
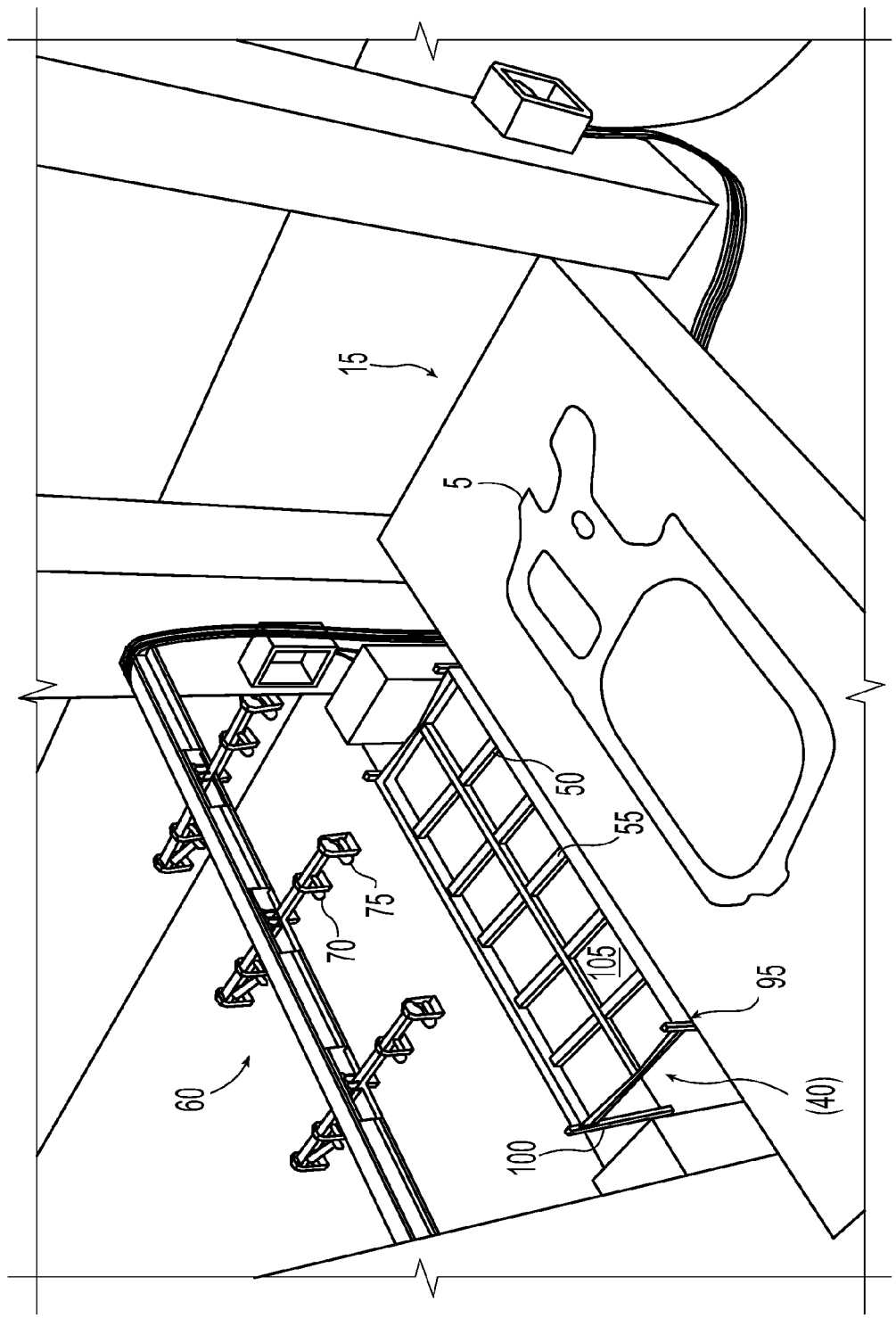
FIG. 3 is an enlarged view of a portion of the transfer press line of FIG. 2.
Figure 4:
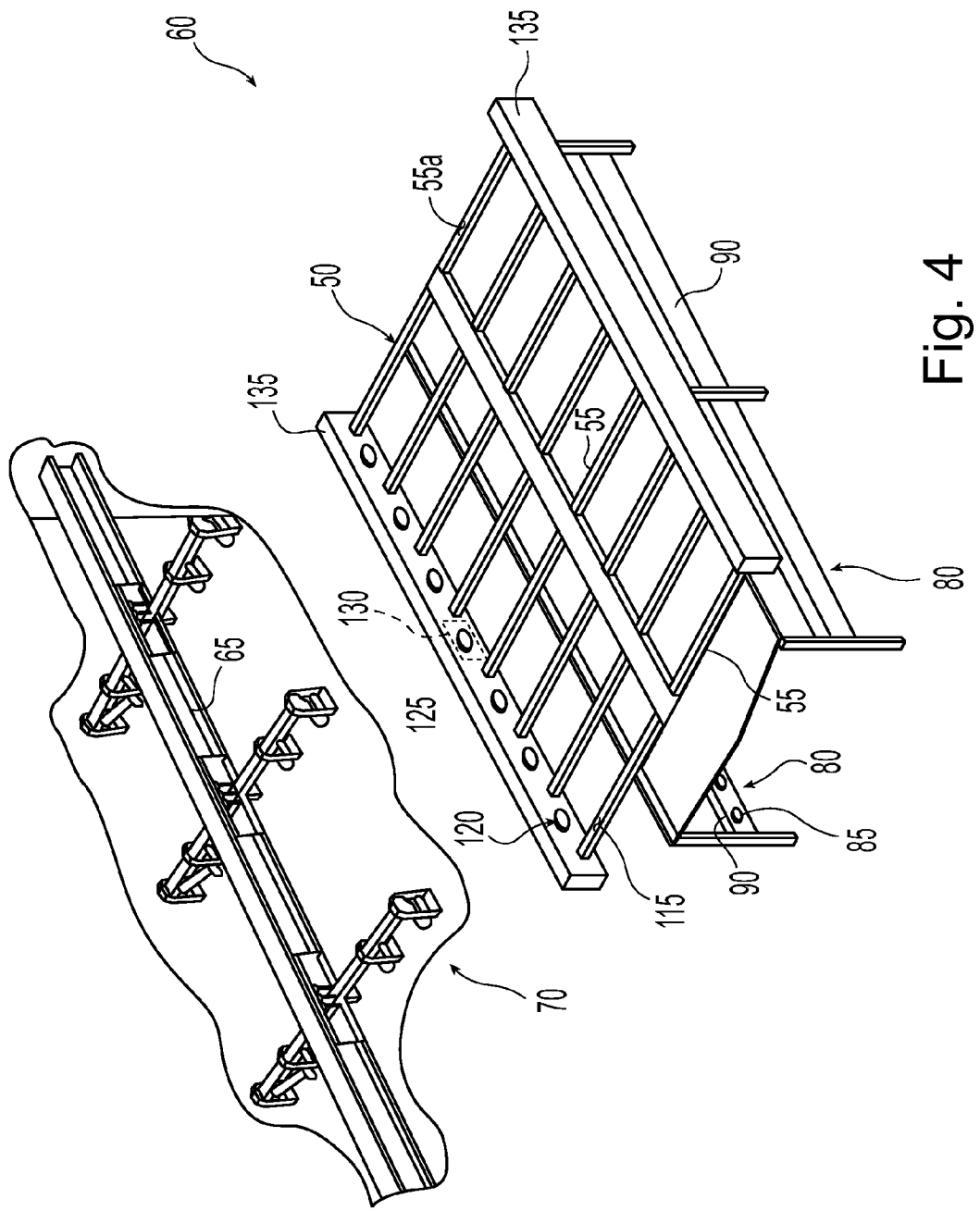
FIG. 4 illustrates various components comprising a crack detection system of this particular exemplary embodiment of the present invention.

More specifically, and as best shown in FIGS. 2-4, an automated crack detection system 60 is installed within an idle station 40 area existing between the draw and trim presses 15, 20 of the transfer press line 10. As can be seen, the idle station 40 exists within a gap 45 between the first, draw press 15, and the second, trim press 20. A support surface 50 extends across this gap to support the body panels 5 as they are moved from the draw press 15 to the trim press 20 during the forming process. In this particular embodiment, the support surface 50 is comprised of a number of spaced apart support members 55—although other designs are also possible.

As most clearly depicted in FIG. 3, an image detector mounting structure 65 is provided to reside above the support members 55, and also above the body panels 5 during the time each is present in the idle station 40. The image detector mounting structure 65 may be comprised of an independent framework, such as that shown, may be comprised of a portion of the press frame(s), or may be some combination thereof. When the image detector mounting structure 65 is an independent framework, it may be self-supporting or attached to one or more portions of the press frame(s).

To the image detector mounting structure 65 are affixed a number of image detectors 70, such as a number of vision sensors (cameras, etc.). The number of image detectors 70 can vary based on the size, shape and/or intricacy of the component(s) to be inspected but, in this particular example, there are 15 vision sensors. It is possible that not all of the image detectors present in a given system of the present invention will be used to detect cracks in all components exposed thereto. That is, in some situations, only a portion of the image detectors may be used.

As stated, the image detectors 70 may various types of vision sensors. Although various types, brands and models of vision sensors may be successfully employed, the VA line of vision sensors available from IPD in Billerica, Mass. has proven effective.

In this case, the image detectors 70 are preferably located on the image detector mounting structure 65 so as to provide complete coverage of the body panel 5 to be inspected. The location of each image detector 70 may be fixed, or it may be adjustable. For example, one or more image detector of a system of the present invention may be adjustable in position to assist with proper imaging of components of considerably varying shape and/or size. Regardless of the type of image detectors used 70, one or more enclosures 75 may be provided to protect the image detectors from contamination and damage. The image detectors 70 may be further mounted to the image detector mounting structure 65 using vibration dampeners (not shown) to minimize any movement of the image detectors during operation. Such vibration dampeners may be of various type, as would be familiar to one skilled in the art.

One or more lighting devices are provided in the idle station 40 to illuminate the underside of the body panel while it resides at the idle station. For example, lighting devices can be located near to or on the floor on which the press line 10 sits. In this particular embodiment, a first set of lighting devices 80 is mounted to a diffusion table 95 (see below) that resides below the body panel 5. The first set of lighting devices 80 may also be located in other areas below the body panel 5, so long as the output thereof can be properly directed onto the underside of the body panel while the body panel resides on top of the support members 55. Each lighting device 85 or a group of lighting devices of the first set of lighting devices 80, may be protected by a housing or otherwise mounted within an enclosure 90. The enclosure(s) 90 help to prevent damage to the lighting devices 85 from falling debris, as well as to prevent contaminants such as grease and oil from contacting the lighting devices and adversely affecting the light output thereof.

While various types of lighting devices are contemplated for use with a system of the present invention, infrared (IR) type lighting devices have been found to work particularly well. For example, the Linear Array product line from Advanced Illumination in Rochester, Vt. works well for this purpose. When IR type lighting devices are employed, IR filters (not shown) may be provided for the image detectors 70.

Preferably, but not essentially, a diffusion table 95 is located between the first set of lighting devices 80 and the support members 55 that support the body panels 5 while they are located in the idle station 40. While the diffusion table 95 may have a variety of constructions, in the exemplary embodiment shown, the diffusion table comprises a substantially rigid frame 100 between which is supported a translucent or semi-transparent sheet 105. For example, the diffusion table may make use of a polycarbonate plastic material, such as Lexan®. Obviously, one skilled in the art would understand that such a diffusion table 95 could also have a number of other constructions while still performing the same function.

Use of a diffusion table 95 provides for multiple benefits, including but not limited to the creation of a substantially evenly diffused area of light beneath the body panel 5. More particularly, the Lexan® or other suitable material used in the diffusion table 95 acts to distribute light from the first set of lighting devices 80 across its surface, thereby helping to ensure that the intensity and distribution of the light is substantially uniform beneath the entirety of the body panel 5. The diffusion table 95 also serves as a protective cover for further preventing contaminants from contacting the first set of subjacent lighting devices 80. To this end, the diffusion table 95 or portions thereof may also be covered with a removable and preferably disposable material, such as a clear plastic wrap.

As shown in the overhead view of FIG. 5a, however, the support members 55 (or other similar support structure(s)) spanning the idle station gap 45 will prevent light emanating from the first set of subjacent lighting devices 80 from reaching portions of an overlying body panel 5 (as evident from the unlit area 110 spanning the width of the diffusion table in FIG. 5a). Consequently, any body panel cracks located within the unlit area 110 caused by each support member 55 would be substantially undetectable by the image detectors 70.

Various steps may be taken to remedy this situation and, in fact, several additional features are incorporated into this exemplary embodiment for that purpose. First, the top surface 55a of each support member 55 that blocks light from the underside of the body panel 5 is preferably made to be IR illuminating or light reflective, depending on the type of light source that will be used. As the material forming the support members 55 will not typically have such characteristics, the top surface 55a of the support members may have an IR illuminating or light reflecting coating 115 applied thereto, whether by painting, adhering, or otherwise.

As can be best observed in FIG. 4, a second set of lighting devices 120 can then be provided to direct light onto the top surfaces 55a of the support members 55. Obviously, the second set of lighting devices 120 may be located at various positions around or near the perimeter of the body panel 5. In this particular embodiment of the present invention, the second set of lighting devices 120 is mounted to existing press structure 135. However, an independent mounting structure may also be provided for this purpose, or the diffusion table 95 frame may be used.

The second set of lighting devices 120 are preferably distributed and oriented to direct light over all of, or substantially all of, the top surfaces 55a of the support members 55. The individual lighting devices 125 of the second set of lighting devices 120 may be of the same type as, or a different type from, those of the first set of lighting devices 80. In this particular embodiment, the second set of lighting devices 120, like the first set of lighting devices 80, are of the IR variety. Also like the first set of lighting devices 80, the second set of lighting devices 120 may be protected within one or more enclosures 130.

FIG. 5b is an overhead view taken from substantially the same position as that of FIG. 5a, only with the top surfaces 55a of the support members 55 coated with an IR illuminating material and with the second set of lighting devices 120 directing light thereon. As can be seen, the unlit area 110 previously appearing in the inspection area (across the diffusion table) as a result of the support member 55 has been eliminated. Rather, there is now a substantially uniform distribution of light visible to the image detectors 70 across the previously unlit area 110, a change which will also be repeated at each location of a support member 55. Therefore, the blocked areas 110 previously attributable to the support members 55 have been made to effectively disappear, and the entire underside of the body panel 5 is sufficiently viewable by the image detectors 70. This allows the system 60 of the present invention to detect cracks in virtually any location on the body panels 5 if desired.

Figure 6:
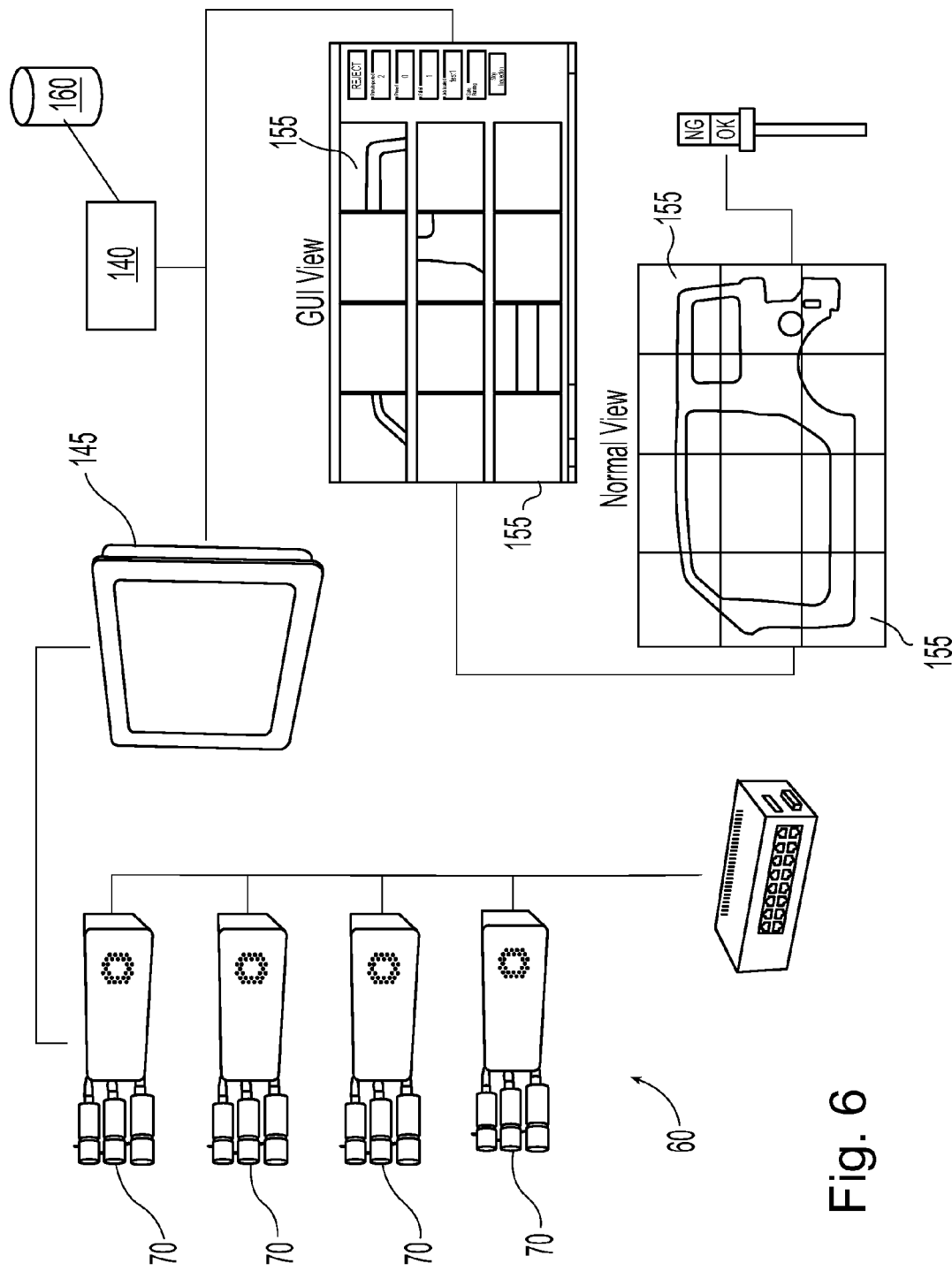
FIG. 6 represents the way in which a component is viewed by the exemplary embodiment of the present invention shown in FIG. 4.
Figure 7:
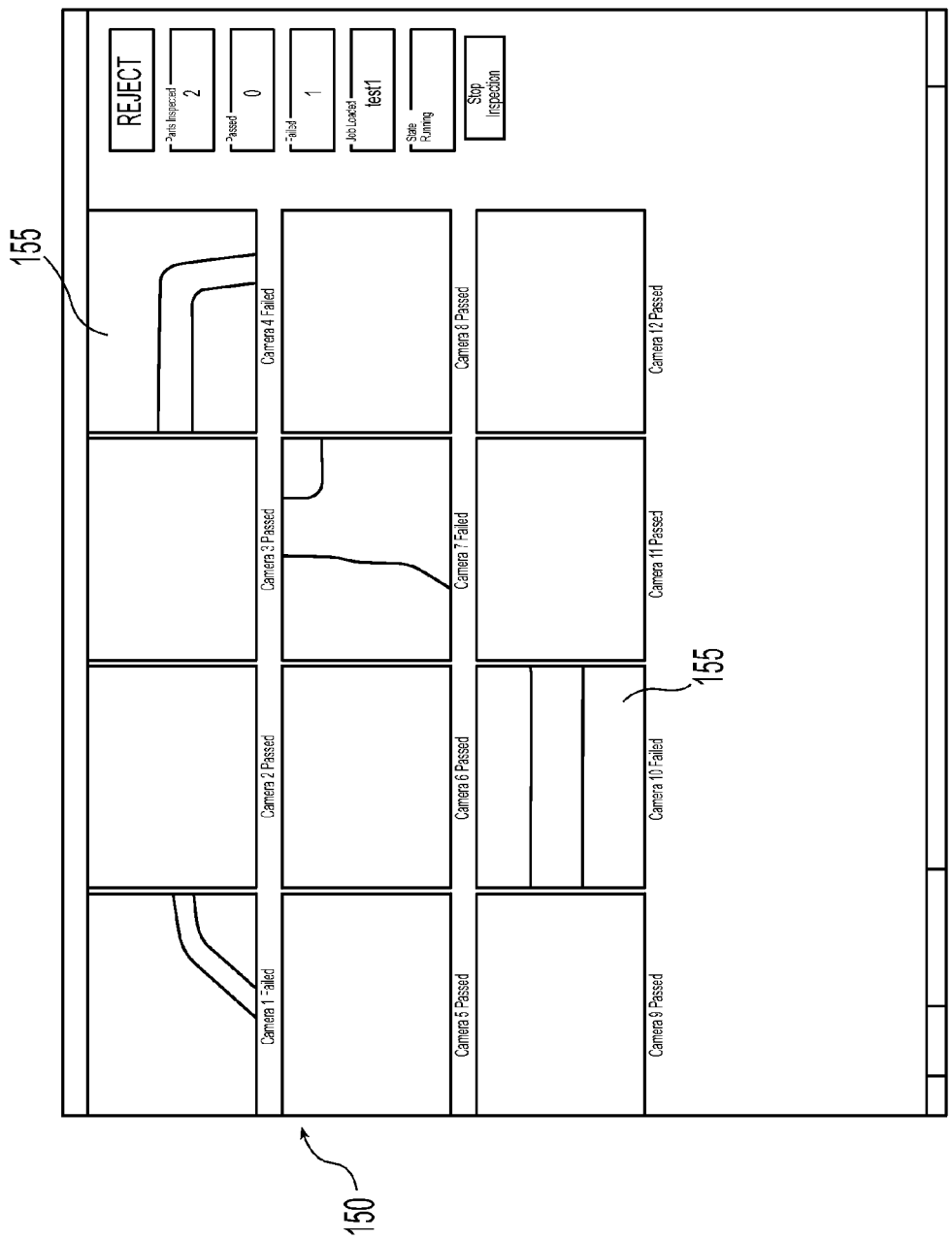
FIG. 7 depicts a first sample user interface screen that may be associated with a software portion of the present invention.
Figure 8:
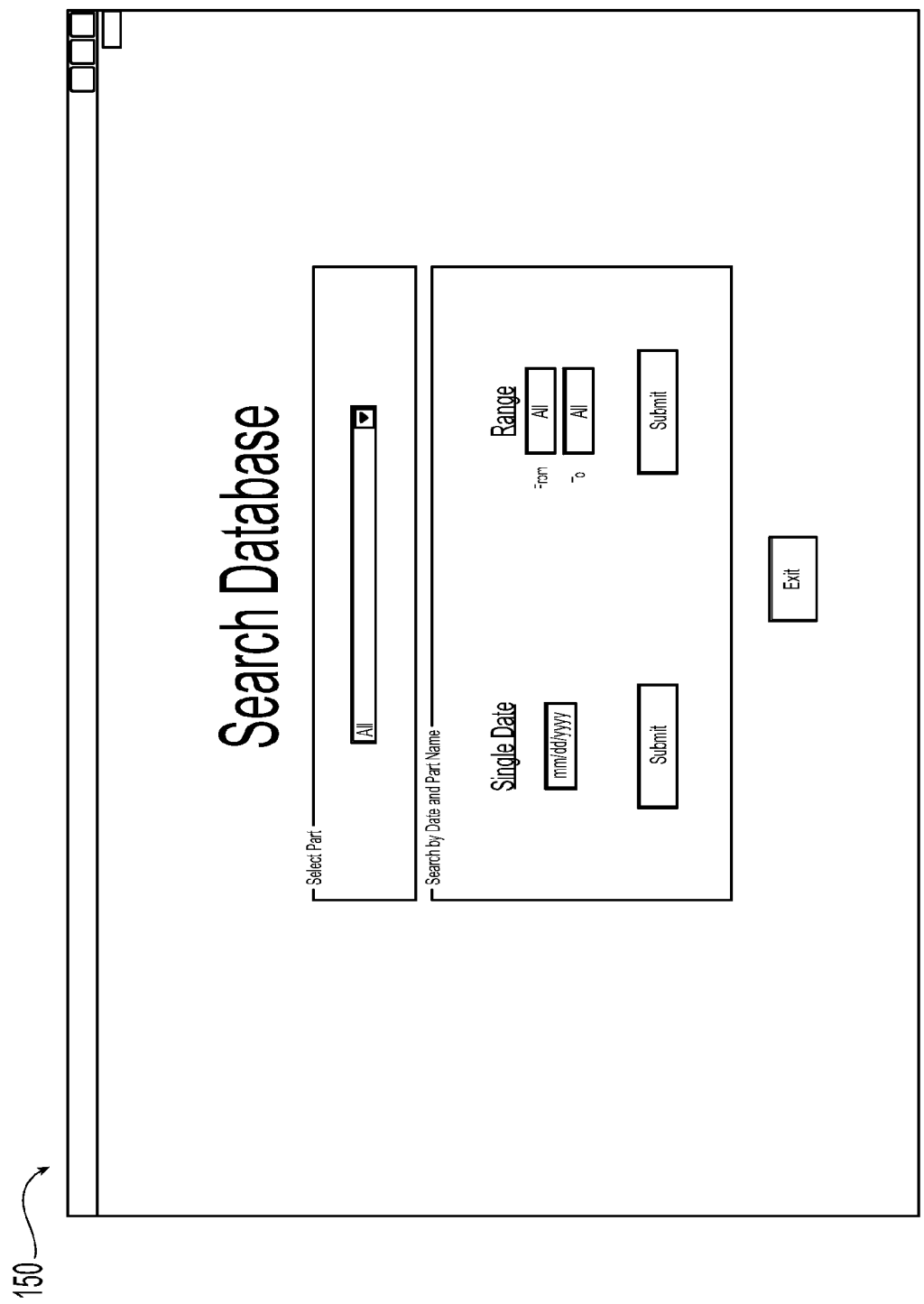
FIG. 8 illustrates a second sample user interface screen that may be associated with a software portion of the present invention.

As can be seen in FIGS. 6-8, embodiments of the present invention are preferably controlled by a processor 140 in communication with specialized software. For example, the processor 140 may be a PC or other processing device, and may be loaded with the software and connected to the system 60. The software may operate to set up the image detectors 70 and to perform various other functions. For example, the system 60 may use the image detectors 70 to periodically check the diffusion table 95 for debris that might negatively affect imaging, and to thereafter alert the system user or engage an optional automated table cleaning device (not shown) if such debris is detected.

In general, a system of the present invention operates by first obtaining a master image of a good (non-cracked) body panel (or other component). Then, during component inspection, the image detectors 70 capture and compare images 155 of subsequently produced body panels (or other components) to the master image to determine if any cracks are present. As shown in FIG. 6, each image detector 70 may capture only a portion of the overall body panel, with images from all of the image detectors then assembled to display the complete panel. Cracks are detected when one or more of the image detectors 70 detects light that is visible through or that passes through a portion of the body panel 5. A plurality of different components may be inspected for cracks using the present invention, as an inventory of numerous master images may be maintained.

Preferably, a system of the present invention includes a display monitor 145 and the software includes a user interface 150 through which images 155 captured by the image detectors may be displayed. It is contemplated that the images 155 may be viewed in various ways, such as one overall image (see FIG. 6) created from the output of the individual image detectors. Alternatively, and as also shown in FIGS. 6 and 7, only a select number of images 155 and, therefore, only a corresponding portion of a component may be viewed at one time. For example, it is possible that instead of displaying an entire body panel, only cameras detecting a crack(s) will produce an image on a display monitor 145. In this case, the user may have the ability to scroll through images from all of the image detectors displaying an image. In yet another embodiment, only a single image (and component portion) may be displayed at one time. The user may also be able to enlarge or otherwise zoom in on areas in the image which may show cracks. A variety of other display strategies may also, of course, be employed. Regardless of the selected display methodology, a system of the present invention allows for cracks in the body panels to be detected and for the cracks to be displayed for viewing by the user.

As best illustrated in FIGS. 6 and 8, the software may perform other functions, such as the archival in a database 160 of crack images related to various different components. Other information related to the cracks may also be stored in a database, such as the date and time the crack(s) occurred. Preferably, the user interface allows a user of the system to search the database(s) for such information. Such searches may be based on, for example only, part name or date(s). The software may also allow a user to create charts or graphs based on historical or currently gathered information.

Several actions may be automatically initiated by a system of the present invention upon detection of one or more cracks. For example, if a crack(s) is found in a single body panel, the system may simply alert the operator thereto. If a similar crack(s) is found in two or more consecutive body panels, the system may send an alarm message to the user indicating that the stamping process should be halted, or may automatically halt the stamping process on its own. Of course, the system could also be programmed to send an alarm message or shut down the stamping process as the result of crack detection in a single panel, three consecutive panels, or virtually any such criteria established by the user.

Panels identified by a system of the present invention as having crack(s) may be removed at the end of the stamping process. However, such panels may also be removed during a resulting halt in the stamping process. For example, it is contemplated that cracked panels may be removed during inspection and/or adjustment to a die(s). It is also contemplated that automated panel handling equipment (not shown) may be provided to remove cracked panels at some point prior to their exit from a press or press line.

As can be understood from the foregoing, a system and method of the present invention can be highly beneficial with respect to the identification of cracked components, and to the reduction of scrap. For example, in the exemplary embodiment shown and described with particularity herein, use of the system and the location thereof allows for the detection of cracks without having to produce the substantial number of defective body panels that would typically be required.

An additional benefit of a system and method of the present invention relates to the ability to compare component images and the ability to archive such images and retrieve them at a later date. Thus, for example, if a crack is occurring in a particular area of a particular component, the database of archived images may be searched to investigate whether such cracks had appeared previously. If so, the database may also contain information related to the correction of the cracks (e.g., specific die work, etc.) In a similar manner, the system and method of the present invention may aid die builders, technicians, maintenance personnel and the like with not only repairing dies, but also with initial die development. More specifically, the system and method of the present invention can be used to archive part quality during die run-off, so that the responsible personnel can more clearly observe any cracking problems and differences in part quality resulting from die modifications.

While a particular exemplary embodiment of the present invention is described in detail in above, it should be apparent to one skilled in the art that many modifications can be made thereto without departing from the scope of the invention. For example, and without limitation, a system and method of the present invention can be installed to a different type of press or to a different transfer press line, the system may be installed at a different location with respect to a press or press line, different image detectors and/or lighting devices may be employed, and the system and method may be used to detect cracks in components unrelated to vehicle manufacturing. Further, as should also be obvious, a system and method of the present invention may be used to detect cracks in non-stamped products. As such, the scope of the invention is not to be considered limited by such disclosure, and modifications are possible without departing from the spirit of the invention as evidenced by the following claims:

What is claimed is:

1. A system for the automatic in-line detection of cracks in components made by stamping:
   a support structure for supporting each component from an underside thereof as it resides at an inspection location;
   one or more first lighting devices located and oriented to direct the output thereof at said underside of said component and through gaps in said support structure;
   an infrared illuminating or light reflecting surface on a top surface of said support structure;
   one or more second lighting devices located and oriented to direct the output thereof at least partially at said illuminating or light reflecting top surface of said support structure so as to illuminate the underside of an overlying portion(s) of said component;
   one or more image detectors for imaging said component from a top side as it is simultaneously illuminated from said underside by said lighting devices; and
   a processor in communication with software and collectively operable to compare one or more images of said component with one or more master images;
   wherein light from the underside of said component will be transferred through or be visible through any cracks therein; and
   wherein cracks are detectable as a difference between a current image and a corresponding master image.

2. The system of claim 1, further comprising a diffusion table residing between said one or more first lighting devices and said support structure.

3. The system of claim 2, wherein said diffusion table includes a translucent or semi-transparent portion that acts to distribute light from said lighting devices across its surface.

4. The system of claim 1, further comprising a means for alerting a user to the presence of one or more cracks in a component.

5. The system of claim 1, further comprising a database for storing a plurality of component images.

6. The system of claim 5, wherein said database is searchable.

7. The system of claim 1, further comprising a display means by which one or more images of a component being inspected are visible to a user of said system.

8. The system of claim 1, wherein one or more of said first and/or said second lighting devices are located within a protective enclosure.

9. The system of claim 1, wherein one or more of said image detectors are located within a protective enclosure.

10. A system for the automatic in-line detection of cracks in components made by a progressive stamping process:
    a support structure comprising a plurality of spaced apart support members for supporting each component from an underside thereof as it resides at an idle station between adjacent transfer presses;
    a first set of lighting devices located below said support members and oriented to direct light at said underside of said component and through gaps between said support members;
    an infrared illuminating or light reflecting surface on a top surface of at least those portions of said support members that underlie said component;
    a second set of lighting devices located outside a perimeter of said component and oriented to direct light at least partially onto said infrared illuminating or light reflecting top surfaces of said support members so as to cause the illumination of the underside of an overlying portion(s) of said component;
    a diffusion table located between said first set of lighting devices and said support members, said diffusion table operable to distribute light from said lighting devices across its surface so as to form a substantially uniform area of lighting beneath said component;
    a plurality of image detectors for imaging said component from a top side as it is simultaneously illuminated from said underside by said lighting devices; and
    a processor in communication with software and collectively operable to compare one or more images of said component captured by said image detectors with one or more master images;
    wherein light from the underside of said component will be transferred through or be visible through any cracks therein; and
    wherein cracks are detectable as a difference between a current image of said component and a corresponding master image.

11. The system of claim 10, wherein said diffusion table includes a translucent or semi-transparent portion housed within a framework.

12. The system of claim 10, further comprising a means for alerting a user to the presence of one or more cracks in a component.

13. The system of claim 10, further comprising a database for storing a plurality of component images.

14. The system of claim 13, wherein said database is searchable.

15. The system of claim 10, further comprising a display means by which one or more images of a component being inspected are visible to a user of said system.

16. The system of claim 10, wherein one or more lighting devices of said first and/or second set of lighting devices is located within a protective enclosure.

17. A method for the automatic in-line detection of cracks in components made by a progressive stamping process:
    providing a support structure comprising a plurality of spaced apart support members for supporting each component from an underside thereof as it resides at an idle station between adjacent transfer presses;
    locating a first set of lighting devices below said support members, said lighting devices oriented to direct light at said underside of said component and through gaps between said support members;
    creating an infrared illuminating or light reflecting surface on a top surface of at least those portions of said support members that underlie said component;
    locating a second set of lighting devices outside a perimeter of said component, said lighting devices oriented to direct light at least partially onto said infrared illuminating or light reflecting top surfaces of said support members so as to cause the illumination of the underside of an overlying portion(s) of said component;
    placing a diffusion table between said first set of lighting devices and said support members, so as to form a substantially uniform area of lighting beneath said component by causing the distribution of light across the surface of said diffusion table;
    employing a plurality of image detectors to image said component from a top side as it is simultaneously illuminated from said underside by said lighting devices;
    using a processor and software in communication therewith to compare one or more images of said component captured by said image detectors with one or more master images;
    recognizing differences between a current image of said component and a corresponding master image caused by the transfer of light through said component; and
    when such differences are discovered, alerting a user to the presence of a crack(s) in said component.

18. The method of claim 17, wherein said diffusion table includes a translucent or semi-transparent portion housed within a framework.

19. The method of claim 17, further comprising providing a database for storing a plurality of component images.

20. The method of claim 19, wherein said database is searchable.

21. The method of claim 17, further comprising providing a display means by which one or more images of a component being inspected are visible to a user of said system.

22. The method of claim 17, further comprising locating one or more lighting devices of said first and/or second set of lighting devices within a protective enclosure.

* * * * *